(12) United States Patent
Eberhardt

(10) Patent No.: US 6,350,282 B1
(45) Date of Patent: *Feb. 26, 2002

(54) STENTED BIOPROSTHETIC HEART VALVE

(75) Inventor: Carol E. Eberhardt, Fullerton, CA (US)

(73) Assignee: Medtronic, Inc., Minneapolis, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/570,373

(22) Filed: Dec. 11, 1995

Related U.S. Application Data

(63) Continuation of application No. 08/231,603, filed on Apr. 22, 1994, now abandoned.

(51) Int. Cl.[7] .................................................. A61F 2/24
(52) U.S. Cl. ...................................... 623/2.13; 623/2.14
(58) Field of Search .......................... 623/2, 900, 2.13, 623/2.14, 2.15, 2.16, 2.17, 2.18, 2.19

(56) References Cited

U.S. PATENT DOCUMENTS

| | | | | |
|---|---|---|---|---|
| 3,365,728 A | * | 1/1968 | Edwards et al. | 623/2 |
| 4,035,849 A | * | 7/1977 | Angell et al. | 623/2 |
| 4,106,129 A | * | 8/1978 | Carpentier et al. | 623/2 |
| 4,345,340 A | * | 8/1982 | Rosen | 623/2 |
| 4,451,936 A | | 6/1984 | Carpenter | |
| 4,506,394 A | * | 3/1985 | Bedard | 623/2 |
| 4,626,255 A | * | 12/1986 | Reichart et al. | 623/2 |
| 4,629,459 A | * | 12/1986 | Ionescu et al. | 623/2 |
| 4,692,164 A | * | 9/1987 | Dzemeshkevich | 623/900 |
| 4,816,029 A | * | 3/1989 | Penny, III et al. | 623/2 |
| 5,037,434 A | | 8/1991 | Lane | 623/2 |
| 5,163,955 A | * | 11/1992 | Love et al. | 623/2 |
| 5,258,021 A | | 11/1993 | Duran | 623/2 |
| 5,258,023 A | * | 11/1993 | Reger | 623/2 |
| 5,376,112 A | * | 12/1994 | Duran | 623/2 |

FOREIGN PATENT DOCUMENTS

| | | | |
|---|---|---|---|
| GB | 2136533 | * | 9/1984 |
| WO | WO90/117738 | | 10/1990 |
| WO | WO93/04643 | | 3/1993 |

* cited by examiner

*Primary Examiner*—Michael Milano
(74) *Attorney, Agent, or Firm*—Thomas G. Berry; Daniel W. Latham

(57) ABSTRACT

A supported bioprosthetic heart valve is provided. The valve includes a stent and a bilogical valve member. The stent has an annular frame defined by a support rail. The support rail is formed to define a triad of axially-projecting circumferentially-spaced commissure posts, each post having an inverted U-shaped configuration and a pair of legs. Each of the pair of legs has an upper end and a lower end. The lower end of each leg merges smoothly with the lower end of a leg of an adjacent commissure post. A sleeve having an inflow end and an outflow end is fitted around the annular frame. The biological valve member is defined by a tubular wall and three leaflets, the three leaflets being attached to the tubular wall and axially converging along three commissures. The biological valve member has a shape which fits the contour of the support rail and is disposed under the support rail. The biological valve member is sutured to the support rail and the outflow end of the sleeve. The bioprosthetic valve member also includes a suturing cuff which is not rigidly attached to the support rail allowing the valve to expand and contract in the lateral direction. The suturing cuff is formed by wrapping the inflow end of the sleeve around a ring-shaped cushion and suturing the sleeve to itself encapsulating thus the ring-shaped cushion. An inflow support ring may also be provided within the suturing cuff for added lateral support.

17 Claims, 5 Drawing Sheets

STENTED BIOPROSTHETIC HEART VALVE

This application is a continuation of application Ser. No. 08/231,603 filed on Apr. 22, 1994, now abandoned.

FIELD OF THE INVENTION

The present invention relates generally to artificial heart valves, and more particularly, is directed to a stented bioprosthetic heart valve.

BACKGROUND OF THE INVENTION

Diseased heart valves may either be repaired through surgical techniques or replaced with an artificial valve. Although reconstructive surgery has been shown to be superior to valve replacement, it is difficult to perform and is not always possible in every patient. The vast majority of patients have their valves replaced with artificial valves. There are two basic types of artificial valves. The first type of artificial valve, called herein a "prosthetic" valve, is typically made of metal or a plastic material. The second type of artificial valve, called herein a "bioprosthetic" valve, comprises a prosthetic device and biological tissue. Both types of valves come in different shapes and diameters depending upon the particular valve being replaced (e.g., mitral, aortic, tricuspid, or pulmonary) and the size of the individual patient's heart. For example, a typical artificial aortic valve has an orifice opening of approximately 19–29 mm in diameter and a typical artificial mitral valve has an orifice opening of 23–35 mm in diameter.

The bioprosthetic valves comprise a biological valve member which is typically an animal heart valve. The biological valve member is defined by a tubular wall having an approximate thickness of 1.5 mm and three flexible leaflets integrally connected to the tubular wall which converge axially along three commissures. The biological valve member may be a bovine pericardium or a porcine aortic valve which is chemically treated. The porcine aortic valve is generally used for all valve replacements in the human heart. The size of the porcine aortic valve may vary, however, depending on the type of valve being replaced in the patient (e.g., mitral, aortic, tricuspid, or pulmonary) and the size of the individual patient's heart.

Bioprosthetic valves are divided into two broadly defined classes. The first class of bioprosthetic valves are stented having a frame (or stent) to which the biological valve member is attached. The biological valve members are sutured to the stent which provides support for the valve member in the patient's body. The stent prevents the biological valve member from collapsing and simplifies the insertion of the valve into the annulus of the patient after excision of the diseased valve. The stented bioprosthetic valves imitate the natural action of heart valves and provide a structure which is relatively compatible with the cardiovascular system.

The second class of bioprosthetic heart valves are stentless and thus do not have a frame. Rather, the biological valve member is sutured to a flexible cloth material. The hemodynamics of a stentless valve more closely approximates that of a natural heart valve. A drawback of a stentless valve, however, is that it is more difficult to implant into the patient than a stented valve. Furthermore, a stentless valve can be collapsed and deformed by the action of the heart because it has no support structure. The action of the heart muscles on this type of valve can fold the valve material and create unexpected stress risers which can eventually lead to failure.

The stented bioprosthetic valves are believed to have important clinical advantages over mechanical non-tissue prosthetic valves. Reports on the use of bioprosthetic valves indicate that the risks of thromboembolism are lower, the need for long-term anticoagulation is minimized, and the nature of occasional valve failure is progressive, thereby permitting elective reoperation under optimal conditions.

Known stented bioprosthetic valves comprise a frame defined by a support rail which is made of either a steel alloy or thermoplastic material, and a plastic wall. The support rail has a circular cross-section and is formed to define three commissure posts supporting the three leaflets of the biological valve member. The plastic wall conforms to the shape of the support rail defined by the three commissure posts providing a rigid support in the lateral direction. The support rails are typically flexible, but not elastic, because the commissure posts are relatively rigid. As the valve leaflets move from open to closed positions, bending stresses occur in the portion of the support rail connecting the commissures. However, the commissure posts themselves do not bend significantly.

The frame is typically covered with a padded, gusseted and porous covering to facilitate attachment, tissue invasion, and encapsulation. A sleeve of porous biocompatible cloth is fitted about the frame and is loosely stitched thereto. Thereafter, a support ring having insert elements which may be portions of a plastic web is positioned outside of the sleeve between each of the commissure posts. The sleeve is trimmed and secured by stitching to the margins of the insert elements. A covering of porous biocompatible cloth is then fitted about the stent, completely enclosing the frame and inserts. The support ring is thus rigidly attached to the frame making the valve inflexible in the lateral direction. A padded suturing rim is formed about the outer periphery of the stent by either folding the cloth upon itself or enclosing an annulus of resilient foam or sponge rubber with the cloth covering.

The cloth layers are typically formed of porous woven or knitted Teflon or Dacron. The insert elements are formed from a sheet or sheets of polyglycol terephthalate (Mylar) although other biocompatible materials such as polypropylene may be used.

The insert elements serve as gussets for increasing the axial dimensions of the stent in the zones between the commissure posts and for providing an attachment surface for the cloth and the biological valve member. Each insert element of the connected series is typically provided with apertures through which stitching is extended during fabrication of the stent.

With the prior art bioprosthetic valves, the biological tissue making up the biological valve member is stitched to the inner wall of the stent. This construction reduces the overall opening through which blood can flow through the valve. The overall thickness of the stented bioprosthetic valve wall is therefore equal to the sum of the thicknesses of the frame wall and the covering mounted thereon which is approximately 1.5 mm (3 mm in cross-section) and the thickness of the tubular wall of the biological valve member which is approximately 1.5 mm (3 mm in cross-section) for a total thickness of approximately 6 mm in cross-section. Thus, with the prior art stented bioprosthetic valves the overall cross-sectional opening of the replaced valve is 6 mm smaller than the patient's natural heart valve. Accordingly, the blood flowing through the bioprosthetic valve is forced through a smaller area than would ordinary flow through a natural valve thus forcing the heart to work harder to circulate the blood through the patient's body. Furthermore, this reduced opening has a greater risk of becoming blocked than a healthy natural valve.

Recent efforts have been made to reduce the overall thickness of the valve wall. These efforts have only concentrated on reducing the thickness of the stent wall. However, the thickness of the stent wall can only be reduced so much before the stent loses its structural integrity. No efforts have been made to reduce the thickness component due to the biological valve member.

The present invention is directed to overcoming or at least minimizing some of the problems mentioned above.

SUMMARY OF THE INVENTION

In the embodiment of the invention disclosed herein, a supported bioprosthetic heart valve is provided. The valve includes a stent and a biological valve member. The stent has an annular frame defined by a support rail. The support rail is formed to define a triad of axially-projecting circumferentially-spaced commissure posts. Each commissure post has an inverted U-shaped configuration having a rounded upper end and a pair of legs. Each of the pair of legs has an upper end and a lower end. The lower end of each leg merges smoothly with the lower end of a leg of an adjacent commissure post. The biological valve member has an inflow end and an outflow end, defined by a tubular wall and three leaflets, the three leaflets being attached to the tubular wall and axially converging along three commissures. The outflow end of the biological valve member is disposed under the support rail and has a shape which fits the contour of the support rail. A sleeve having an inflow end and an outflow end is fitted around the annular frame. The inflow end of the sleeve is sutured to the inflow end of the biological valve member and the outflow end of the end of the sleeve is sutured to the support rail and the outflow end of the biological valve member.

The bioprosthetic heart valve also includes a suturing cuff which is not rigidly attached to the support ring allowing the valve to expand and contract in the lateral direction. The suturing cuff is formed by wrapping the inflow end of the sleeve around a ring-shaped cushion and suturing the sleeve to itself thus encapsulating the ring-shaped cushion. An inflow support ring may also be encapsulated with the ring-shaped cushion by the sleeve for added support. In another embodiment, the suturing cuff is formed by wrapping the inflow end of the sleeve upon itself and suturing the sleeve in place. In this latter embodiment, neither the ring-shaped cushion nor the inflow support ring are used.

BRIEF DESCRIPTION OF THE DRAWINGS

The foregoing and other features of the present invention will be best appreciated with reference to the detailed description of a specific embodiment of the invention, which follows when read in conjunction with accompanying drawings, wherein.

Figure 1:
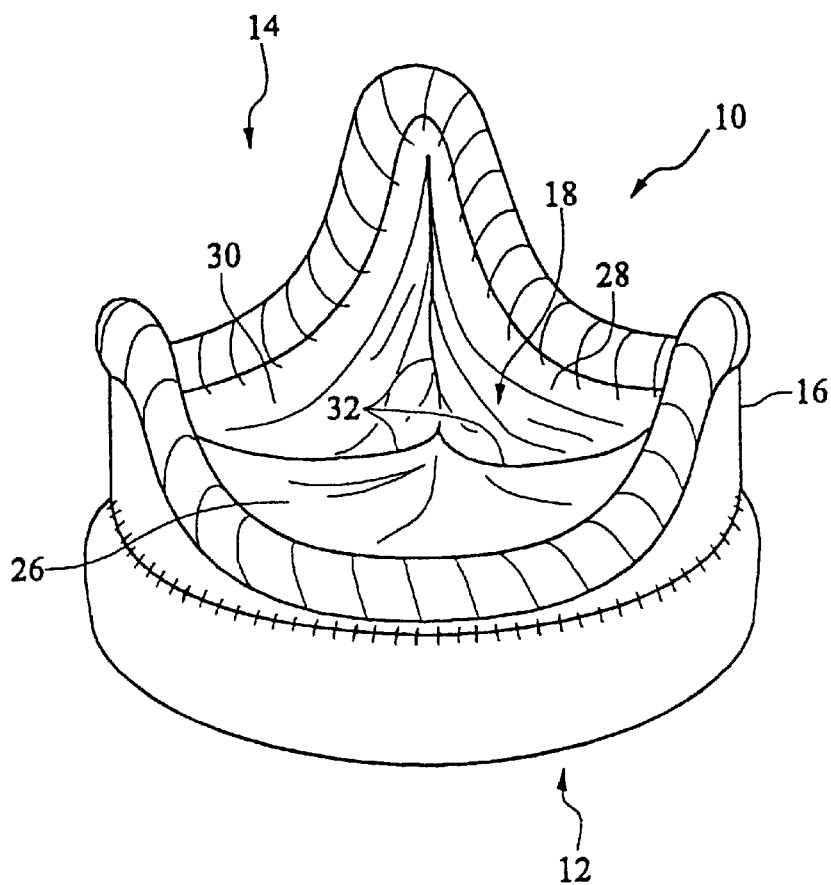
FIG. 1 is a perspective view of a bioprosthetic heart valve according to the present invention.

While the present invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the appended claims.

DETAILED DESCRIPTION OF A SPECIFIC EMBODIMENT OF THE INVENTION

Turning now to the drawings and referring initially to FIG. 1, a bioprosthetic valve adapted for implantation in the mitral position is shown generally by reference numeral 10. Whether the valve is adapted for replacement of a natural mitral valve, aortic valve, tricuspid valve or pulmonary valve, depends on the size of the valve and the construction of its suturing cuff or ring. With respect to the present invention, all four types of valves have the same essential features and, therefore, a mitral valve has been selected for illustration purposes only.

The valve 10 has an inflow portion 12 and an outflow portion 14. The valve 10 includes a stent 16 and a biological valve member 18. The biological valve member 18 has an inflow end 17 and an outflow end 19 and is defined by a tubular wall 20, having an inner surface 22 and an outer surface 24 (shown in FIG. 7) and leaflets 26, 28, and 30 which are integrally attached to the inner surface of the tubular wall. The leaflets 26, 28 and 30 converge axially along commissures 32. Although in the embodiment illustrated valve 10 has three leaflets and three commissures, it should be understood that the concept disclosed herein would be equally applicable to a valve having two or more leaflets and commissures.

Figure 2:
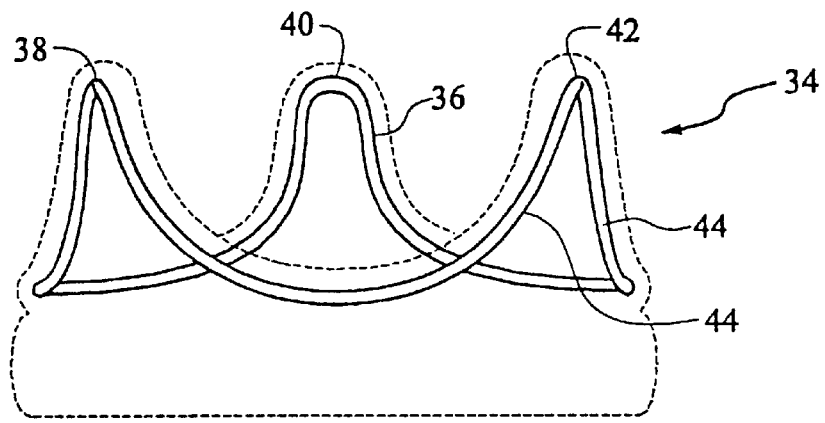
FIG. 2 is a perspective view of a support rail for the valve shown in FIG. 1.

The stent 16 includes a flexible frame 34 which may be made of a thin wire or contoured thermoplastic material, e.g., polypropylene, celcon or acetyl homopolar. The flexible frame 34 shown in FIG. 2 is defined by a support rail 36. The flexible frame 34 is generally annular in configuration having a diameter of 17–35 mm depending on the size and type of valve being replaced. The support rail 36 forming the flexible frame 34 has a triad of axially-projecting and circumferentially-spaced commissure posts 38, 40 and 42. The commissure posts 38, 40 and 42 project upwardly in the direction of the outflow portion 14 of the valve 10. As shown in FIG. 2, each commissure post is generally of an inverted U-shaped configuration having legs 44. Each leg 44 merges smoothly at its lower end with a leg of an adjacent commissure post.

The support rail 36 is generally circular in cross section and is of substantially uniform diameter throughout its entire extent. The diameter of the support rail 36 is approximately 1 mm. Each inverted U-shaped commissure post has a rounded or smoothly-curved upper end. The lower ends of the legs 44 of the commissure posts curve outwardly and merge smoothly with the lower ends of adjacent legs, as shown in FIG. 2. The support rail 36 may be formed of any spring material which is non-corrosive, fatigue resistant, and biocompatible. Stainless steel, a titanium alloy, other alloys having similar properties or a thermoplastic material might be used. If stainless steel or an alloy is used, the support rail 36 can serve as a radio paque marker which can be detected from outside the body.

Figure 4:
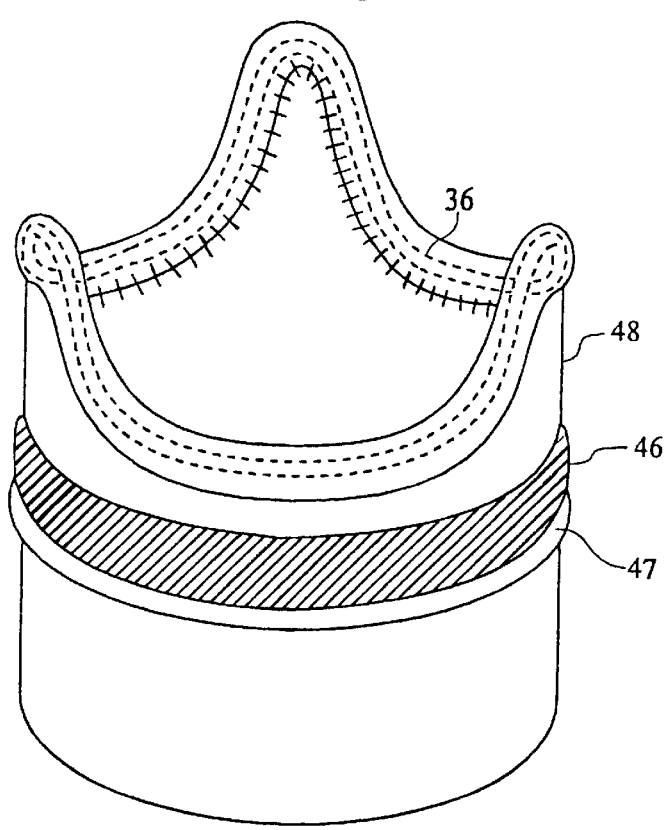

The stent 16 also includes a generally ring-shaped cushion 46 disposed at the inflow portion 12 of the valve 10, as shown in FIG. 4. The cushion 46 is preferably formed of felt, silicone, or a foam material. The stent 16 may also include an inflow support ring 47 (shown in FIG. 4) also disposed at the inflow portion 12 of the valve 10 for added support. The inflow support ring 47 is preferably formed of non-corrosive, fatigue resistant and biocompatible material.

Figure 3:
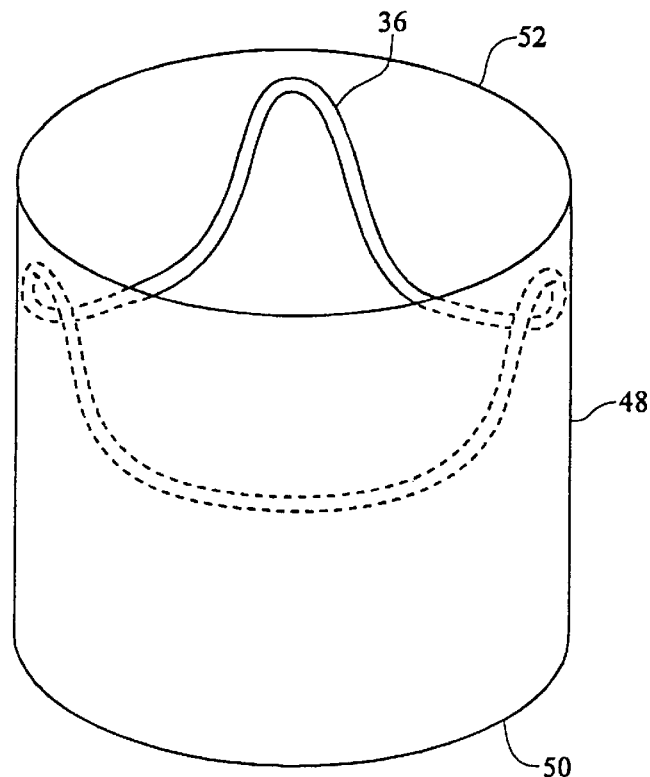
FIGS. 3–6 are perspective views illustrating steps in the fabrication of one embodiment of the bioprosthetic valve according to the present invention.
Figure 5:
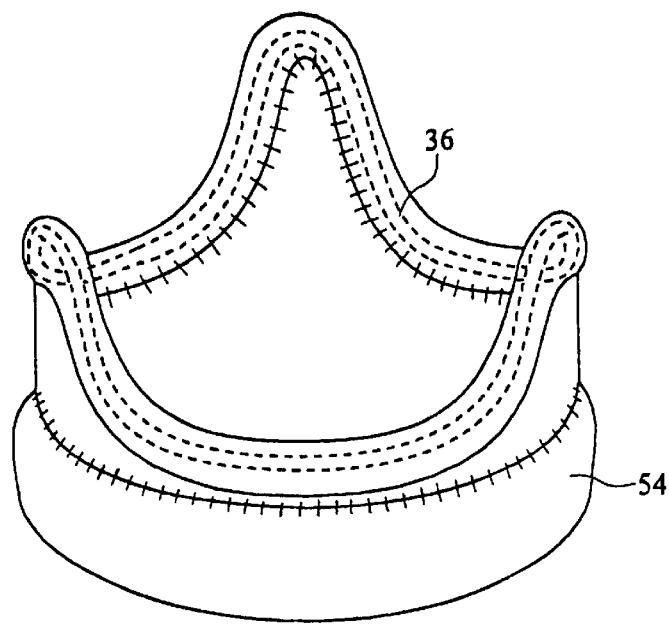

FIGS. 3–6 illustrate the steps in the fabrication of the completed valve 10. First, the stent 16 is constructed. This is accomplished by first fitting a sleeve 48 of porous biocompatible fabric, having an inflow end 50 and an outflow end 52, around the support rail 36, as shown in FIG. 3. Next, the outflow end 52 of the sleeve 48 is folded over the support rail 36. The outer portion of the sleeve 48 is then sutured to the folded portion along the perimeter of the support rail 36, as shown in FIG. 4. Next, the cushion 46 and the inflow support ring 47 are placed around the inflow end 50 of the sleeve 48, as shown in FIG. 4. The inflow end 50 of the sleeve 48 is folded around the cushion 46 and inflow support ring 47 and then sutured to itself encapsulating the cushion and inflow support ring thereby forming a suturing cuff 54, as shown in FIG. 5.

Figure 4A:
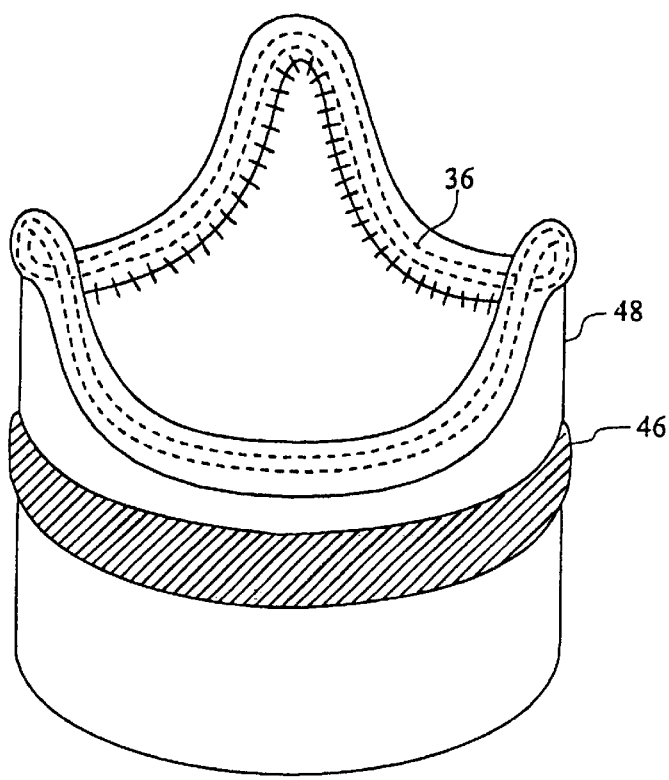
FIG. 4A is perspective view illustrating the step shown in FIG. 4 in the fabrication of an alternate embodiment of the bioprosthetic valve according to the present invention.
Figure 4B:
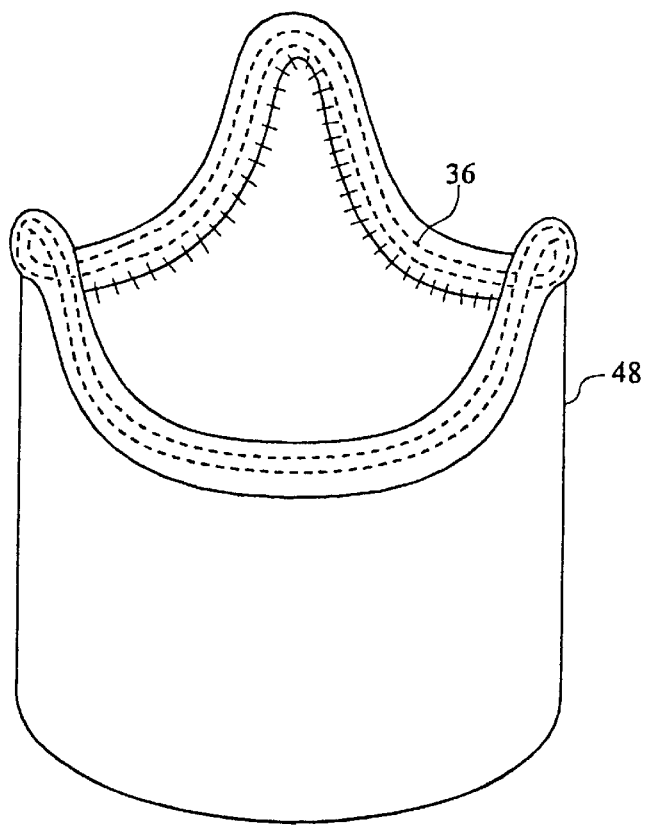
FIG. 4B is a perspective view illustrating the step shown in FIG. 4 in the fabrication of yet another embodiment of the bioprosthetic valve according to the present invention.

FIG. 4A shows the fabrication of an alternate embodiment of the valve 10 where the suturing cuff 54 is formed without the inflow support ring 47. FIG. 4B shows the fabrication of another alternate embodiment of the valve 10 where the suturing cuff 54 is formed by folding the inflow end 50 of the sleeve 48 upon itself and stitching the sleeve in place. In this embodiment, the suturing cuff 54 is formed without the ring-shaped cushion 46 or the inflow support ring 47.

The suturing cuff 54 forms a liquid tight seal between the bioprosthetic valve 10 and the annulus of the patient preventing blood from leaking through the valve. At the same time, the suturing cuff 54 is porous so that it can be sutured to the annulus of the patient and allow the in growth of tissue into the fabric. Because the suturing cuff 54 is not integrally formed and rigidly attached to the flexible frame 34, as with the prior art devices, the valve 10 is permitted to flex, i.e., expand and contract, in the lateral direction. This provides greater flexibility for the biological valve member 10 making it less susceptible to failure in the lateral direction.

Figure 6:
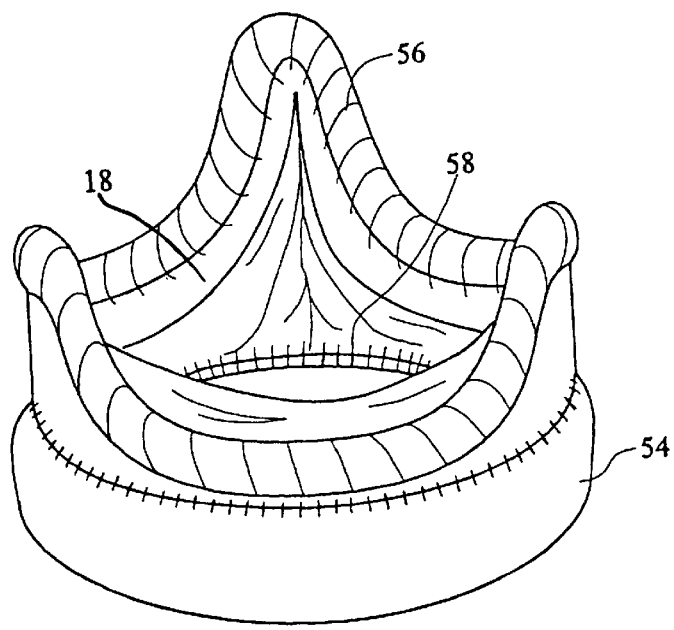
Figure 7:
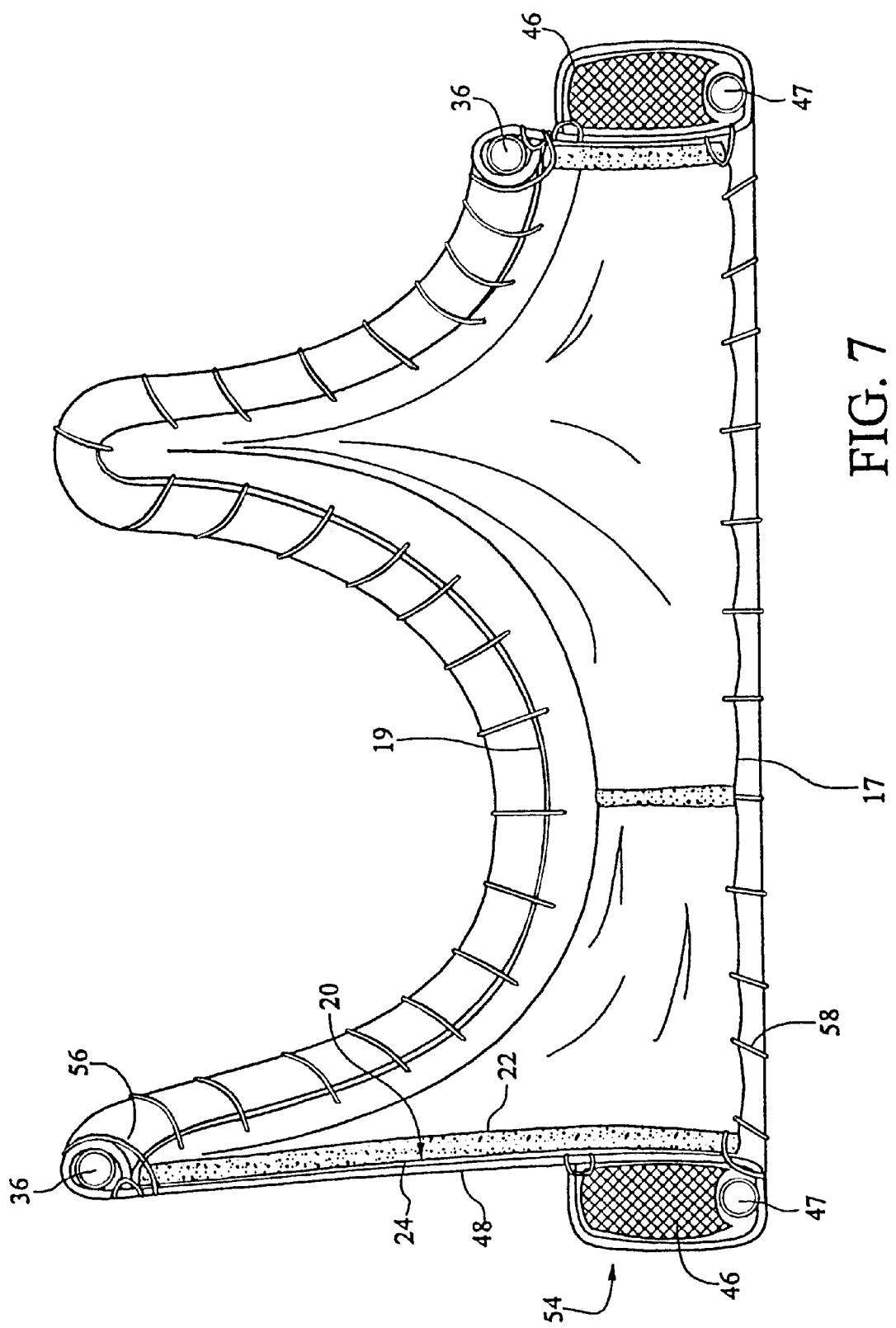
FIG. 7 is a vertical sectional view of a completed bioprosthetic mitral valve according to the present invention.

Next, the biological valve member 18 is mounted to the stent 12. Prior to mounting, the biological valve member 18 is trimmed so that it conforms to the contour of the support rail 36. Once trimmed, the biological valve member 18 is fitted under the support rail 36. The outflow end 19 of the biological valve member 18 is then sutured to the support rail 36 and the sleeve 48 along the perimeter of the support rail, as shown in FIGS. 6 and 7. The stitch is made by sewing a suture 56 through the tubular wall 20 of the biological valve member 18, out through the sleeve 48, around the support rail 36 and back through the tubular wall.

The inflow end 17 of the biological valve member 18 is then stretched and folded under itself so that the folded portion is sandwiched in between the tubular wall 20 and the inner layer of the inflow end 50 of the sleeve 48. The inflow end 17 of the biological valve member 18 is then sutured to the inner layer of the inflow end 50 of the sleeve 48, as shown in FIG. 6. The stitch is made by sewing a suture 58 through both layers of the inflow end 17 of the biological valve member 18, through the inner layer of the inflow end 50 of the sleeve 48 and back out the sleeve 48 as best seen in FIG. 7. A stitch known as a "box stitch" is particularly suitable for this purpose. It should be understood by those of ordinary skill in the art, however, that other methods may be used in constructing the completed valve 10.

By suturing the biological valve member 18 under the support rail 36, the tubular wall 20 is integrated into the stent wall rather than attached adjacent to it as with prior stented valves. Accordingly, the thickness of the valve wall is equal to the thickness of the tubular wall 20, which is approximately 1.5 mm, plus the thickness of the two layers of the sleeve 48 (since it is folded over itself), which is approximately 0.5 mm (0.25 mm for each layer), for a total thickness of approximately 2.0 mm. Since the biological valve member 18 is secured beneath the support rail 36 rather than adjacent to it, the thickness of the support rail, which is less than the thickness of the tubular wall 20 (approximately 1 mm), is not added to the overall thickness of the valve wall. Therefore, by eliminating the thickness of the support rail 36 from the thickness of the stent wall, the overall thickness of the valve wall is reduced by approximately 2.0 mm in the cross-sectional direction.

This construction provides a significant advantage over the prior art. By reducing the thickness of the valve wall by approximately 2.0 mm, the opening of the valve 10 is correspondingly increased by 2.0 mm. This allows blood to flow through the valve 10 more freely than with prior art devices and hence reduces the chance of blockage. Also, the heart does not have to work as hard to force blood through the valve 10 as it does with prior art valves having smaller openings. The valve 10, therefore, has the superior hemodynamics of a stentless valve, while offering the ease of implantation associated with a stented valve.

FIG. 7 illustrates details of the completed valve with the biological valve member 18 secured under the support rail 36 by sutures 56. The configuration and location of the suturing cuff 54 is particularly suited for use of the valve as a mitral valve replacement. The valve 10 illustrated in FIG. 7 can be adapted for replacement of the aortic, tricuspid or pulmonary valve with minor modification as those of ordinary skill in the art will appreciate. By modifying the shape and position of the suturing cuff 54 and as well as the dimensions of the valve members taking into account those differences occasioned by the anatomical characteristics of those portions of the human heart to which the respective valves are to be secured, the valve illustrated in FIG. 7 can be used for replacement of any human heart valve.

I claim:

1. A supported bioprosthetic heart valve having an inflow and and outflow side, the heart valve comprising:

a) a stent having an annular frame defined by a support rail, the support rail having an inflow and an outflow side corresponding to the inflow and outflow sides of the heart valve, the annular frame defining relatively exterior and interior directions;

b) a biological valve member defined by a tubular wall and a plurality of leaflets, the plurality of leaflets being attached to the tubular wall and axially converging along commisures of the plurality of leaflets, the biological valve member extending
   i) from the outflow side of the heart valve toward the outflow side of the heart valve and ending at the inflow side of the support rail; and
   ii) not extending around the support rail; and c) a sleeve fitted around and tangentially exterior to the annular frame, the sleeve having an inflow end and an outflow end, the outflow end being folded interiorly over the support rail and secured to the support rail along the entire annular perimeter of the support rail such that a recess is formed along the entire annular perimeter of the support rail directly underneath the support rail, the sleeve also secured to the biological valve member such that an outflow end of the tubular wall of the biological valve member is secured to the sleeve within the recess directly underneath the entire annular perimeter of the support rail and whereby the overall thickness of the valve wall at the tubular wall of the biological valve member includes the thickness of the biological valve member and the sleeve and does not include the thickness of the support rail.

2. The supported bioprosthetic heart valve of claim 1, in which the inflow end of the sleeve is folded upon itself and sutured in place to form a suturing cuff.

3. The supported bioprosthetic heart valve of claim 1, further comprising a ring shaped cushion disposed around the sleeve at the inflow end.

4. The supported bioprosthetic heart valve of claim 3, in which the inflow end of the sleeve is wrapped around the ring-shaped cushion and sutured to itself to encapsulate the ring-shaped cushion and form a suturing cuff.

5. The supported bioprosthetic heart valve of claim 3, further comprising an inflow support ring disposed around the sleeve at the inflow end adjacent to the ring-shaped cushion.

6. The supported bioprosthetic heart valve of claim 5, in which the inflow end of the sleeve is wrapped around the ring-shaped cushion and the inflow support ring and sutured to itself to encapsulate the ring-shaped cushion and inflow support ring to form a suturing cuff.

7. The supported bioprosthetic heart valve of claim 1, in which the support rail comprises a triad of axially-projecting circumferentially-spaced commissure posts, each commissure post having an inverted U-shaped configuration comprising a rounded upper end and a pair of legs, each of the pair of legs comprising an upper end and a lower end, the lower end of each leg curving outwardly and merging smoothly with the lower end of a leg of an adjacent commissure post.

8. The supported bioprosthetic heart valve of claim 1 wherein the folded sleeve is secured to the support rail along a perimeter of the support rail by suturing an outer portion of the sleeve to the folded portion of the sleeve.

9. The supported bioprosthetic heart valve of claim 1 wherein the tubular wall of the biological valve member is secured to the sleeve within the recess by a suture through the tubular wall of the biological valve member, around the support rail and back through the tubular wall.

10. A supported bioprosthetic heart valve having an inflow and an outflow side, the heart valve comprising:

a) a stent having an annular frame defining relatively exterior and interior directions, and including a support rail, the support rail having a contour defined by a triad of axially-projecting circumferentially-spaced commissure posts, the support rail having an inflow and an outflow side corresponding to the inflow and outflow sides of the heart valve;

b) a biological valve member having an inflow end and an outflow end, a tubular wall and three leaflets, the three leaflets being attached to the tubular wall and axially converging along three commissures, the tubular wall of the biological valve member extending from the inflow side of the heart valve toward the outflow side of the heart valve and ending at the inflow side of the support rail in a shape that conforms to the shape of the support rail, but not extending around, the support rail; and c) a sleeve fitted around and tangentially exterior to the annular frame, the sleeve having an inflow end and an outflow end, the outflow end being folded interiorly over the support rail and secured to the support rail along the entire annular perimeter of the support rail such that a recess is formed along the entire annular perimeter of the support rail directly underneath the support rail, the sleeve also secured to the biological valve member such that an outflow end of the tubular wall of the biological valve member is secured to the sleeve within the recess directly underneath the entire annular perimeter of the support rail and whereby the overall thickness of the valve wall at the tubular wall of the biological valve member includes the thickness of the biological valve member and the sleeve and does not include the thickness of the support rail.

11. The supported bioprosthetic heart valve of claim 10, in which the inflow end of the sleeve is folded upon itself and stitched in place to form a cuff that is not rigidly attached to the support rail so that the valve may expand and contract in a lateral direction.

12. The support bioprosthetic heart valve of claim 10, further comprising a ring-shaped cushion disposed around the sleeve at the inflow end.

13. The supported bioprosthetic heart valve of claim 12, in which the inflow end of the sleeve is wrapped around the ring-shaped cushion and sutured to itself to encapsulate the ring-shaped cushion and form a suturing cuff that is not rigidly attached to the support rail so that the valve may expand and contract in a lateral direction.

14. The supported bioprosthetic heart valve of claim 12, further comprising an inflow support ring disposed around the sleeve at the inflow end adjacent to the ring-shaped cushion.

15. The supported bioprosthetic heart valve of claim 14, in which the inflow end of the sleeve is wrapped around the ring-shaped cushion and the inflow support ring and is sutured to itself to encapsulate the ring-shaped cushion and inflow support ring and form a supported suturing cuff that is not rigidly attached to the support rail so that the valve may expand and contract in a lateral direction.

16. The supported bioprosthetic heart valve of claim 10 wherein the folded sleeve is secured to the support rail along a perimeter of the support rail by suturing an outer portion of the sleeve to the folded portion of the sleeve.

17. The supported bioprosthetic heart valve of claim 10 wherein the tubular wall of the biological valve member is secured to the sleeve within the recess by a suture through the tubular wall of the biological valve member, around the support rail and back through the tubular wall.

* * * * *